United States Patent [19]

Winter et al.

[11] 4,439,565
[45] Mar. 27, 1984

[54] OLIGOMERIC ESTERAMIDES CONTAINING PENDANT HINDERED AMINE GROUPS

[75] Inventors: Roland A. E. Winter, Armonk; Roger F. Malherbe, Yonkers, both of N.Y.; Frank Tieh-Yin Fu, Taipei, Taiwan

[73] Assignee: Ciba-Geigy Corporation, Ardsley, N.Y.

[21] Appl. No.: 440,490

[22] Filed: Nov. 10, 1982

[51] Int. Cl.$^3$ .................. C07D 401/12; C07D 401/14; C08K 5/34
[52] U.S. Cl. ...................... 524/103; 525/186; 525/419; 528/341; 546/190
[58] Field of Search ................ 524/103; 525/186, 419; 528/341; 546/190

[56] References Cited

U.S. PATENT DOCUMENTS

| | | | |
|---|---|---|---|
| 3,272,776 | 9/1966 | Caldwell | 528/335 |
| 4,086,207 | 4/1978 | Cassandrini et al. | 524/100 |
| 4,210,612 | 7/1980 | Karrer | 525/204 |
| 4,232,131 | 11/1980 | Rody et al. | 525/184 |
| 4,233,410 | 11/1980 | Rody et al. | 525/123 |
| 4,233,412 | 11/1980 | Rody et al. | 525/167 |
| 4,234,700 | 11/1980 | Rody et al. | 525/55 |
| 4,234,707 | 11/1980 | Rody et al. | 524/103 |
| 4,276,401 | 6/1981 | Karrer | 526/263 |
| 4,294,949 | 10/1981 | Karrer | 526/262 |
| 4,331,586 | 5/1982 | Hardy | 525/186 |
| 4,344,876 | 8/1982 | Berner | 525/186 |
| 4,348,524 | 9/1982 | Karrer et al. | 546/187 |

OTHER PUBLICATIONS

H. J. Heller et al., Pure and Appld. Chem., 36, 141 (1973).

Primary Examiner—Lorenzo B. Hayes
Assistant Examiner—R. A. White
Attorney, Agent, or Firm—Luther A. R. Hall

[57] ABSTRACT

Oligomeric esteramides having recurring structural units of the formula

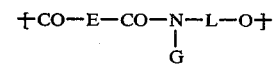

where G is a hindered amine radical of formula I or II

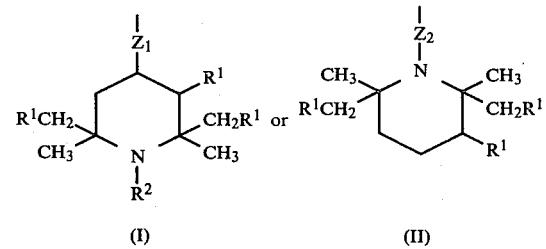

in which $R^1$ is hydrogen or alkyl having 1 to 4 carbon atoms, $R^2$ is hydrogen, alkyl having 1 to 12 carbon atoms, allyl, benzyl, acetyl, acryloyl or cyano, $Z_1$ is a direct bond, $-NHCH_2CH_2-$, $-NHCH_2CH_2CH_2-$ or $-OCH_2CH_2-$, $Z_2$ is ethylene or trimethylene, E is a divalent aliphatic, aromatic or alicyclic radical and L is unsubstituted or substituted alkylene, are useful light stabilizers for plastics.

23 Claims, No Drawings

OLIGOMERIC ESTERAMIDES CONTAINING PENDANT HINDERED AMINE GROUPS

BACKGROUND OF THE INVENTION

The present invention relates to homopolymers and copolymers containing pendant hindered amine groups which are useful as light and heat stabilizers for organic materials and to stabilized compositions containing said copolymers.

The hindered amine compounds having the 2,2,6,6-tetra-substituted piperidinyl structure have long been known as effective light stabilizers for organic materials and have enjoyed considerable commercial success.

Such hindered amine light stabilizers are described in detail by H. J. Heller and H. R. Blattmann, Pure and Applied Chemistry, 36, 141–161 (1973).

It is known that bistetramethylpiperidin-4-yl sebacate improves very much the stability to light of polypropylene. Simple derivatives of tetramethylpiperidine are relatively volatile compounds and tend to volatilize at the processing temperature and during prolonged outdoor storage of the stabilized plastic.

In U.S. Pat. Nos. 4,210,612 and 4,294,949 homopolymeric and certain copolymeric compounds having pendant hindered amine moieties are described as useful light stabilizers. The homopolymers are those made by the free radical polymerization of acryloyl or methacryloyl derivatives of compounds containing hindered amine moieties.

Copolymers of acryloyl or methacryloyl substituted hindered amine monomers with acryloyl or methacryloyl monomers containing light absorbing moieties such as the benzophenones, benzotriazoles, α-cyanocinnamates or benzalmalonates are described in U.S. Pat. No. 4,276,401 as being useful light stabilizers for organic materials.

Polymeric derivatives, which are still well soluble in the particular plastic, but remain in the plastic on exposure to heat, provide valuable stabilizers. Examples thereof are polyureas such as described in U.S. Pat. Nos. 4,233,410 and 4,086,207, polyesters such as described in U.S. Pat. No. 4,233,412, polycarbonates such as described in U.S. Pat. No. 4,234,700 or polyamides such as described in U.S. Pat. No. 4,232,131.

The present invention relates to novel oligomeric esteramides which are useful for improving the stability to light, heat and oxidation of plastics.

DETAILED DISCLOSURE

This invention pertains to oligomeric esteramides containing pendant hindered amine groups which are useful as light and heat stabilizers for organic materials and to stabilized compositions containing said copolymers.

More particularly, the oligomeric esteramides of this invention are homopolymeric or copolymeric and have recurring structural units, joined in essentially random fashion, of the formula (A)

$$\mathrm{\{CO-E_1-CO-N-L-O\}_n\{CO-E_2-CO-N-L-O\}_m} \quad (A)$$
$$\phantom{xxxxxxxx}|\phantom{xxxxxxxxxxxxxxxxx}|$$
$$\phantom{xxxxxxxx}G\phantom{xxxxxxxxxxxxxxxxx}G$$

wherein
G is a hindered amine radical of formula I or II (I) and (II) structures shown in which $R^1$ is hydrogen or alkyl having 1 to 4 carbon atoms, $R^2$ is hydrogen, alkyl having 1 to 12 carbon atoms, allyl, benzyl, acetyl, acryloyl or cyano, $Z_1$ is a direct bond, —NHCH$_2$CH$_2$—, —NHCH$_2$CH$_2$CH$_2$— or —OCH$_2$CH$_2$—, with the heteroatom attached to the piperidyl ring, $Z_2$ is ethylene or trimethylene, $E_1$ and $E_2$ are the same or different and are alkylene having 2 to 12 carbon atoms, o-phenylene, m-phenylene, p-phenylene, 5-norbornen-2,3-diyl or vinylene, L is ethylene, trimethylene or —CH$_2$CHR$^3$— where $R^3$ is alkyl having 1 to 6 carbon atoms, cycloalkyl having 5 or 6 carbon atoms or phenyl, and the sum of n plus m is 2 to 50, preferably 2 to 10.

When $E_1$ and $E_2$ are the same, the oligomeric esteramide is derived from two components only and is homopolymeric in nature. The ratio of n/m is not significant in this situation where a homopolymeric structure is involved.

When $E_1$ and $E_2$ are different, the oligomeric esteramide is derived from two diacid components and is copolymeric in nature. The ratio of n/m in such cases is from 49/1 to 1/49, preferably 9/1 to 1/9.

The numbers n and m indicate the average degree of polymerization and their sum of 2 to 50 indicates the oligomeric nature of the instant esteramides. The molecular weight of the esteramides range from about 400 to about 10,000. The molecular weights of the oligomers are determined by gel permeation chromatography.

Depending on the chemical structure as well as the molecular weight, the esteramides are brittle or soft resins, or viscous oils which flow at room temperatures.

$R^1$ can be hydrogen or alkyl of 1 to 4 carbon atoms such as methyl, ethyl, isopropyl or n-butyl. Preferably $R^1$ is hydrogen or methyl.

$R^2$ is hydrogen, alkyl of 1 to 12 carbon atoms, such as methyl, ethyl, isopropyl, n-butyl, n-hexyl, 2-ethylhexyl, n-decyl or n-dodecyl, allyl, benzyl, acetyl, acryloyl or cyano. Preferably $R^2$ is hydrogen, methyl, propyl, allyl, benzyl or acetyl.

$Z_1$ is a direct bond, —NHCH$_2$CH$_2$—, —NHCH$_2$CH$_2$CH$_2$— or —OCH$_2$CH$_2$—, with the heteroatom attached to the piperidyl ring. Preferably $Z_1$ is a direct bond, NHCH$_2$CH$_2$— or —OCH$_2$CH$_2$—.

$Z_2$ is ethylene or trimethylene, but is preferably ethylene.

G is preferably the hindered amine radical of formula I.

$E_1$ and $E_2$ are alkylene of 2 to 12 carbon atoms such as ethylene, trimethylene, tetramethylene, hexamethylene, octamethylene or decamethylene. Preferably $E_1$ and $E_2$ are alkylene of 2 to 8 carbon atoms.

$E_1$ and $E_2$ are also o-phenylene, m-phenylene, p-phenylene, 5-norbornen-2,3-diyl or vinylene. Preferably $E_1$ and $E_2$ are o-phenylene, m-phenylene or p-phenylene.

Preferably $E_1$ and $E_2$ are the same and the instant esteramides are homopolymeric in nature.

L is ethylene, trimethylene or —$CH_2CHR^3$— where $R^3$ is alkyl of 1 to 6 carbon atoms, such as methyl, ethyl, n-butyl or n-hexyl; cycloalkyl of 5 or 6 carbon atoms such as cyclopentyl or cyclohexyl; or phenyl. Preferably L is ethylene, trimethylene, propylene (where $R^3$ is methyl) or styrolene (wherein $R^3$ is phenyl).

The instant oligomeric esteramides can be prepared by reacting a dicarboxylic acid di-lower-alkyl ester (preferably dimethyl ester) III $$\text{lower alkyl—OCO—E—COO—lower alkyl} \qquad \text{(III)}$$

with an aminoalcohol of formula IV or V.

(IV)　　　　　　　　(V)

The aminoalcohol IV can be prepared by hydroxyalkylation of the corresponding primary amine. Another method is the reductive amination of the 4-oxo-piperidine with the appropriate aminoalcohol. Some classes of polyalkylated 4-aminopiperidine derivatives are disclosed in U.S. Pat. Nos. 3,684,765, 3,904,581 and 4,166,813.

The polycondensation is carried out neat or in an inert solvent, such as toluene, xylene, mesitylene, chlorobenzene, in the presence of a suitable catalyst.

Preferred examples of catalysts used are sodium alkoxides, titanium tetralkoxides or lithium amide. The ratio between reactants of formula IV and V and diesters of formula III is preferably 1:1.

The formation of an amide under these conditions was a surprise and could not be predicted. When 4-butylamino-2,2,6,6-tetramethylpiperidine and ethyl caprate were heated for 6 hours at 170° C., no amide was obtained.

Thus, it is assumed that during the polycondensation, the transesterification precedes the intramolecular migration of the carbonyl group from O-to N-atom. Further evidence for this mechanism results from experiments with homolog aminoalcohol IV. For L=ethylene or propylene, a facile polycondensation takes place with III, but when L is pentamethylene, the formation of a diester is observed.

An alternative synthesis requires the N-acylation of IV with the anhydride of a dicarboxylic acid, esterification of the remaining carboxylic group followed by a polycondensation.

The esteramides of this invention are effective light stabilizers in a wide range of polymers. Polymers which can be stabilized include:

1. Polymers which are derived from mono- or diolefins, e.g., polyethylene which can optionally be crosslinked, polypropylene, polyisobutylene, polymethylbutene-1, polymethylpentene-1, polyisoprene, polybutadiene.

2. Mixtures of the homopolymers cited under (1), for example mixtures of polypropylene and polyethylene, polypropylene and polybutene-1, polypropylene and polyisobutylene.

3. Copolymers of the monomers based on the homopolymers cited under (1), for example ethylene/propylene copolymers, propylene/butene-1, copolymers, propylene/isobutylene copolymers, ethylene/butene-1 copolymers as well as terpolymers of ethylene and propylene with a diene, for example hexadiene, dicyclopentadiene or ethylidene norbornene, and copolymers of α-olefins, e.g., ethylene with acrylic or methacrylic acid.

4. Polystyrene.

5. Copolymers of styrene and of α-methylstyrene, for example styrene/butadiene copolymers, styrene/acrylonitrile copolymers, styrene/acrylonitrile/methacrylate copolymers, styrene/acrylonitrile copolymers modified with acrylic ester polymers to provide impact strength as well as block copolymers, e.g., styrene/butadiene/styrene block copolymers.

6. Graft copolymers of styrene, for example the graft polymer of styrene to polybutadiene, the graft polymer of styrene with acrylonitrile to polybutadiene as well as mixtures thereof with the copolymers cited under (5), commonly referred to as acrylonitrile/butadiene/styrene or ABS plastics.

7. Halogen-containing vinyl polymers, for example polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, vinylidene chloride/vinyl acetate copolymers.

8. Polymers which are derived from α,β-unsaturated acids and derivatives thereof, polyacrylates and polymethacrylates, polyacrylic amides and polyacrylonitrile.

9. Polymers which are derived from unsaturated alcohols and amines and from the acyl derivatives thereof or acetals, for example polyvinyl alcohol, polyvinyl acetate, polyvinyl stearate, polyvinyl benzoate, polyvinyl maleate, polyvinyl butyral, polyallyl phthalate, polyallyl melamine and copolymers thereof with other vinyl compounds, for example ethylene/vinyl acetate copolymers.

10. Homopolymers and copolymers which are derived from epoxides, for example polyethylene oxide or the polymers which are derived from bis-glycidyl ethers.

11. Polyacetals, for example polyoxymethylene, as well as polyoxymethylenes which contain ethylene oxide as comonomer.

12. Polyalkylene oxides, for example polyoxyethylene, polypropylene oxide or polybutylene oxide.

13. Polyphenylene oxides.

14. Polyurethanes and polyureas, such as in urethane coatings.

15. Polycarbonates.

16. Polysulfones.

17. Polyamides and copolyamides which are derived from diamines and dicarboxylic acids and/or from aminocarboxylic acids or the corresponding lactams, for example polyamide 6, polyamide 6/6, polyamide 6/10, polyamide 11, polyamide 12, poly-m-phenyleneisophthalamide.

18. Polyesters which are derived from dicarboxylic acids and dialcohols and/or from hydroxycarboxylic acids or the corresponding lactones, for example polyethylene glycol terephthalate, poly-1,4-dimethylolcyclohexane terephthalate.

19. Cross-linked polymers which are derived from aldehydes on the one hand and from phenols, ureas and melamine on the other, for example phenol/formaldehyde, urea/formaldehyde and melamine/formaldehyde resins.

20. Alkyd resins, for example glycerol/phthalic acid resins and mixtures thereof with melamine/formaldehyde resins.

21. Unsaturated polyesters resins which are derived from copolyesters of saturated and unsaturated dicarboxylic acids with polyhydric alcohols as well as from vinyl compounds as cross-linking agents and also the halogen-containing, flame-resistant modifications thereof.

22. Natural polymers, for example cellulose, rubber, as well as the chemically modified homologous derivatives thereof, for example cellulose acetates, cellulose propionates and cellulose butyrates and the cellulose ethers, for example methyl cellulose.

The stabilizing of polyolefins, styrene polymers and polyamides and of polyurethanes is of particular importance, and the instant copolymers are outstandingly suitable for this. Examples of such polymers are high density and low density polyethylene, polypropylene, ethylene/propylene copolymers, polystyrene, styrene/butadiene/acrylonitrile terpolymers, mixtures of polyolefins or of styrene polymers, and polyurethanes based on polyethers or polyesters, in the form of lacquers, filaments, films, sheets, films, elastomers or foams.

The copolymeric stabilizers are added to the plastics in a concentration of 0.05 to 5% by weight, calculated relative to the material to be stabilized. Preferably, 0.1 to 2.5% by weight of the copolymers calculated relative to the material to be stabilized, are incorporated into the latter.

Incorporation can be effected after polymerization, for example by mixing the compounds and, if desired, further additives into the melt by the methods customary in the art, before or during shaping, or by applying the dissolved or dispersed compounds to the polymer, with subsequent evaporation of the solvent if necessary.

The novel copolymers can also be added to the plastics to be stabilized in the form of a master batch which contains these copolymers, for example in a concentration of 2.5 to 25% by weight.

Although the compounds of the invention may be used above to provide a light stabilizing function, the compounds of this invention are often combined with other stabilizers, even other light stabilizers, in the preparation of stabilized compositions. The stabilizers may be used with phenolic antioxidants, pigments, colorants or dyes, light stabilizers such as hindered amines, metal deactivators, etc.

In general, the stabilizers of this invention are employed from about 0.05 to about 5% by weight of the stabilized composition, although this will vary with the particular substrate and application. An advantageous range is from about 0.1 to about 2.5%.

The stabilizers of Formula I may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain from about 0.05 to about 5%, preferably from about 0.1 to about 2.5% by weight of various conventional additives, such as the following, particularly phenolic antioxidants or light-stabilizers, or mixtures thereof:

1. Antioxidants 1.1 Simple 2,6-dialkylphenols, such as, for example, 2,6-di-tert.-butyl-4-methylphenol, 2-tert.-butyl-4,6-dimethylphenol, 2,6-di-tert.-butyl-4-methoxymethylphenol and 2,6-dioctadecyl-4-methylphenol.

1.2 Derivatives of alkylated hydroquinones, such as for example, 2,5-di-tert.-butyl-hydroquinone, 2,5-di-tert.-amyl-hydroquinone, 2,6-di-tert.-butyl-hydroquinone, 2,5-di-tert.-butyl-4-hydroxy-anisole, 3,5-di-tert.-butyl-4-hydroxy-anisole, 3,5-di-tert.-butyl-4-hydroxyphenyl stearate and bis-(3,5-di-tert.-butyl-4-hydroxyphenyl) adipate.

1.3 Hydroxylated thiodiphenyl ethers, such as for example, 2,2'-thio-bis-(6-tert.-butyl-4-methylphenol), 2,2'-thio-bis-(4-octylphenol), 4,4'-thio-bis-(tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxyphenol) disulfide.

1.4 Alkylidene-bisphenols, such as, for example, 2,2'-methylene-bis-(6-tert.-butyl-4-methylphenol), 2,2'-methylene-bis-(6-tert.-butyl-4-ethylphenol), 4,4'-methylene-bis-(6-tert.-butyl-2-methylphenol, 4,4'-methylene-bis-(2,6-di-tert.-butyl-phenol), 2,6-di-(3-tert.-butyl-5-methyl-2-hydroxybenzyl)-4-methylphenol, 2,2'-methylene-bis-[4-methyl-6-(α-methylcyclohexyl)-phenol], 1,1-bis(3,5-dimethyl-2-hydroxyphenyl)-butane, 1,1-bis-(5-tert.-butyl-4-hydroxy-2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecylmercapto-butane, 1,1,5,5-tetra-(5-tert.-butyl-4-hydroxy-2-methylphenyl)-pentane and ethylene glycol, bis-[3,3-bis-(3-tert.-butyl-4-hydroxyphenyl)-butyrate].

1.5 O-, N- and S-benzyl compounds, such as for example, 3,5,3',5'-tetra-tert.-butyl-4,4'-dihydroxydibenzyl ether, octadecyl 4-hydroxy-3,5-dimethylbenzyl-mercaptoacetate, tris-(3,5-di-tert.-butyl-4-hydroxybenzyl)-amine and bis-(4-tert.-butyl-3-hydroxy-2,6-dimethylbenzyl) dithioterephthalate.

1.6 Hydroxybenzylated malonates, such as for example, dioctadecyl 2,2-bis-(3,5-di-tert.-butyl-2-hydroxybenzyl)-malonate, dioctadecyl 2-(3-tert.-butyl-4-hydroxy-5-methylbenzyl)-malonate, di-dodecylmercapto-ethyl 2,2-bis-(3,5-di-tert.-butyl-4-hydroxybenzyl)-malonate and di-[4-(1,1,3,3-tetramethylbutyl)phenyl] 2,2-bis-(3,5-di-tert.-butyl-4-hydroxybenzyl)-malonate.

1.7 Hydroxybenzyl-aromatic compounds, such as, for example, 1,3,5-tri-(3,5-di-tert.-butyl-4-hydroxybenzyl)-2,4,6-trimethyl-benzene, 1,4-di-(3,5-di-tert-butyl-4-hydroxybenzyl)-2,3,5,6-tetramethylbenzene and 2,4,6-tri-(3,5-di-tert.-butyl-4-hydroxy-benzyl)-phenol.

1.8 s-Triazine compounds, such as, for example 2,4-bis-octylmercapto-6-(3,5-di-tert.-butyl-4-hydroxyanilino)-s-triazine, 2-octylmercapto-4,6-bis-(3,5-di-tert.-butyl-4-hydroxy anilino)-s-triazine, 2-octylmercapto-4,6-bis-(3,5-di-tert.-butyl-4-hydroxyphenoxy)-s-triazine, 2,4,6-tris-(3,5-di-tert.-butyl-4-hydroxyphenoxy)-s-triazine, 2,4,6-tris-(3,5-di-tert.-butyl-4-hydroxyphenylethyl)-s-triazine and 1,3,5-tris-(3,5-di-tert.-butyl-4-hydroxybenzyl) isocyanurate. 1.9 Amides of β-(3,5-di-tert.-butyl-4-hydroxyphenyl)-propionic acids, such as, for example 1,3,5-tris-(3,5,-di-tert.-butyl-4-hydroxyphenyl-propionyl)-hexahydro-s-triazine and N,N'-di-3,5-ditert.-butyl-4-hydroxyphenyl-propionyl)-hexamethylenediamine, N,N'-bis-β-(3,5-di-t-butyl-4-hydroxyphenyl)propionyl-hydrazine. 1.10 Esters of β-(3,5-di-tert.-butyl-4-hydroxyphenyl)-propionic acid with monohydric or polyhydric alcohols, such as for example, with methanol, ethanol, octadecanol, 1,6-hexanediol; 1,9-nonanediol, ethylene glycol, 1,2-propanediol, diethylene glycol, thiodiethylene glycol, neopentylglycol, pentaerythritol, 3-thiaundecanol, 3-thia-pentadecanol, trimethylhexanediol, trimethylolethane, trimethylolpropane, tris-hydroxyethyl isocyanurate and 4-hydroxymethyl-1-phospha- 2,6,7-trioxabicyclo-[2.2.2]octane.

1.11 Esters of β-(5-tert.-butyl-4-hydroxy-3-methylphenylpropionic acid with monohydric or polyhydric alcohols, such as for example, with methanol, ethanol, octadecanol, 1,6-hexanediol, 1-9-nonanediol, ethylene glycol, 1,2-propanediol, di- ethylene glycol, thiodiethylene glycol, neopentylglycol, pentaerythritol, 3-thiaundecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2.2.2.]octane.

1.12 Esters of 3,5-di-tert.-butyl-4-hydroxyphenylacetic acid with monohydric or polyhydric alcohols, such as for example, with methanol, ethanol, octadecanol, 1,6-hexanediol, 1,9-nonanediol, ethylene glycol, 1,2-propendiol, diethylene glycol, thiodiethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1phospha-2,6,7-trioxabicyclo-[2.2.2]-octane, especially the tetrakis ester of pentaerythritol.

1.13 Benzylphosphonates, such as, for example, dimethyl 3,5 di-tert.-butyl-4-hydroxybenzylphosphonate, diethyl 3,5-di-tert.-butyl-4-hydroxybenzylphosphonate, dioctadecyl 3,5-di-tert.-butyl-4-hydroxybenzylphosphonate and dioctadecyl 5-tert.-butyl-4-hydroxy-3-methylbenzylphosphonate.

2. Light-stabilizers 2.1 Esters of optionally substituted benzoic acids, e.g., 3,5-di-tert.-butyl-4-hydroxybenzoic acid, 2,4-di-tert.-butyl-phenyl ester or -octadecyl ester or 2-methyl-4,6-di-tert.-butyl-phenyl ester.

2.2 Sterically hindered aminesm e.g., 4-benzoyl-2,2,6,6-tetramethylpiperidine, 4-stearyloxy-2,2,6,6-tetramethylpiperidine, bis-(2,2,6,6-tetramethylpiperidyl)) sebacate, bis-(1,2,2,6,6-pentamethylpiperidyl) sebacate, bis-(1,2,2,6,6-pentamethylpiperidyl) 2-n-butyl-2-(2-hydroxy-3,5-di-tert-butyl-benzyl)malonate or 3-n-octyl-7,7,9,9-tri-methyl-1,3,8-triazaspiro[4.5]decane-2,4-dione.

2.3 Oxalic acid diamides, e.g., 4,4'-di-octyloxy-oxanilide, 2,2'-di-octyloxy-5,5'-di-tert.-butyl-oxanilide, 2,2'-didodecyloxy-5,5'-di-tert.-butyl-oxanilide, 2-ethoxy-2'-ethyloxanilide, N,N'-bis-(3-dimethyl-aminopropyl)-oxalamide, 2-ethoxy-5-tert.-butyl-2'-ethyl-oxanilide and the mixture thereof with 2-ethoxy-2'-ethyl-5,4'-di-tert.-butyl-oxanilide, or mixture of ortho- and para-methoxy- as well as of o- and p-ethoxy-di-substituted oxanilides.

3. Metal deactivators, e.g., oxanilide, isophthalic acid dihydrazide, sebacic acid-bis-phenylhydrazide, bis-benzylidene-oxalic acid dihydrazide, N,N'-diacetal-adipic acid dihydrazide, N,N'-bis-salicyloyl-oxalic acid dihydrazide, N,N'-bis-salicycloylhydrazine, N,N'-bis-(3,5-di-tert.-butyl-4-hydroxyphenylpropionyl)-hydrazine, N-salicyloyl-N'-salicylalhydrazine,-3-salicyloyl-amino-1,2,4-triazole or N,N'-bis-salicyloyl-thiopropionic acid dihydrazide.

4. Basic co-stabilizers, e.g., alkali metal salts and alkaline-earth metal salts of higher fatty acids, for example Ca-stearate, Zn-stearate, Mg-behenate, Na-ricinoleate or K-palmitate.

5. Nucleation agents, e.g., 4-tert.-butylbenzoic acid, adipic acid or diphenylacetic acid.

6. Phosphites and phosphonites, such as, for example, triphenyl phosphite, diphenylalkyl phosphites, phenyldialkyl phosphites, tri-(nonyl-phenyl) phosphite, trilauryl phosphite, trioctadecyl phosphite and 3,9-isodecyloxy-2,4,8,10-tetraoxa-3,9-diphospha-[5.5]-undecane and tetra(2,4-di-tert-butylphenyl)diphenylene-4,4'-bis(phosphonite).

Other additives that can be incorporated in the stabilized compositions are thiosynergists such as dilauryl thiodipropionate, lubricants such as stearyl alcohol, fillers, asbestos, kaolin, talc, glass fibers, pigments, optical brighteners, flameproofing agents and antistatic agents.

While the instant copolymers containing pendant hindered amine moieties G are particularly useful as stabilizers for polymeric substrates, it is also contemplated that said copolymers would provide dyesites for the subsequent dyeing of the stabilized polymer with acid dyes. This would be most beneficial in the dyeing of polyolefins such as polypropylene by the inclusion of the hindered amine basic site into polyolefin fiber.

The following examples are presented for the purpose of illustration only and are not to be construed to limit the nature or scope of the instant invention in any manner whatsoever.

EXAMPLE 1

8.71 g (0.05 mole) of 2-(2,2,6,6-tetramethyl)-4-piperidylamino)-ethanol and 10.02 g (0.05 mole) of dimethyl adipate are heated for 2 hours at 120° C. 0.2 g of titanium (IV) butoxide is added and the temperature is raised slowly to 160° C., methanol being distilled off. The mixture is stirred for a further 8 hours at 190° C. until 1.2 ml of methanol has been collected.

The product is dissolved in 100 ml of tetrahydrofuran and precipitated by addition of hexane. The resulting polyesteramide is dried in vacuo (0.1 mm) for 15 hours; 11.7 g of a semi-solid resin, with an average molecular weight of about 1,000 (by gel permation chromatography (GPC)), is obtained.

EXAMPLE 2

When 25.0 g (0.125 mole) of 2-(2,2,6,6-tetramethyl-4-piperidylamino)-ethanol is reacted with 14.64 g (0.10 mole) of dimethyl succinate and 4,36 g (0.025 mole) of dimethyl adipate, as described in Example 1, 26.0 g of a solid is obtained, m.p. 45°–50° C.

EXAMPLE 3

When 42.0 g (0.20 mole) of 3-(2,2,6,6-tetramethyl-4-piperidylamino)-propan-1-ol is reacted with 34,8 g (0.20 mole) of dimethyl adipate, as described in Example 1, 48.6 g of a yellowish resin is obtained. The average molecular weight is about 700 (by gel permeation chromatography).

EXAMPLE 4

When 55.0 g (0.257 mole) of 1-(2,2,6,6-tetramethyl-4-piperidylamino)-propan-2-ol is reacted with 37.5 g (0.258 mole) of dimethyl succinate, as described in Example 1, 35.0 g of a yellowish solid is obtained, m.p. 49°–54° C.

EXAMPLE 5

When 53.6 g (0.25 mole) of 1-(2,2,6,6-tetramethyl-4-piperidylamino)-propan-2-ol is reacted with 43.5 g (0.25 mole) of dimethyl adipate, as described in Example 1, 69.6 g of a viscous resin is obtained. The average molecular weight, determined by gel permeation chromatography, is about 800.

EXAMPLE 6

21.44 g (0.10 mole) of 1-(2,2,6,6-tetramethyl-4-piperidylamino)-propan-2-ol and 19.50 g (0.10 mole) of dimethyl phthalate are heated for 1 hour at 120° C. 0.7 g of titanium (IV) butoxide is added and the heating continued for 4 hours at 170° C. 5.4 ml of methanol are collected during this period. 100 ml of tetrahydrofuran are added at 60° C. and the mixture is stirred for 2 hours. A white solid is obtained which is filtered, washed with hexane: in a yield of 9.4 g, softening at 135° C., mp 250°–280° C. The average molecular weight determined by gel permeation chromatography is about 700.

EXAMPLE 7

From 21.44 g (0.10 mole) of 1-(2,2,6,6-tetramethyl-4-piperidylamino)-propan-2-ol and 19.50 g (0.10 mole) of dimethyl terephthalate, as described in Example 6, 15.4 g of a white solid is obtained by precipitation from tetrahydrofuran—hexane: mp 61°–72° C.

The average molecular weight is about 850 (by gel permeation chromatography).

EXAMPLE 8

From 21.44 g (0.10 mole) of 1-(2,2,6,6-tetramethyl-4-piperidylamino)-propan-2-ol and 19.50 g (0.10 mole) of dimethyl isophthalate, as described in Example 6. 21.0 g of sticky solid is obtained, mp 50°–60° C., with an average molecular weight of 850 (by gel permeation chromatography).

EXAMPLE 9

When 24.34 g (0.10 mole) of N-(2,2,6,6-tetramethyl-4-piperidyl)-N'-(2-hydroxyethyl)-ethylenediamine are reacted with 14.61 g (0.10 mole) of dimethyl succinate, as described in Example 1, 18.0 g of a light yellow solid are obtained, mp 130°–150° C. The average molecular weight determined by gel permeation chromatography is 1900.

EXAMPLE 10

When 41.60 g (0.171 mole) of N-(2,2,6,6-tetramethyl-4-piperidyl)-N'-(2-hydroxyethyl)-ethylenediamine are reacted with 29.68 g (0.171 mole) of dimethyl adipate, as described in Example 1, 57.5 g of a low melting resin are obtained, the average weight being about 1,000 by gel permeation chromatography.

EXAMPLE 11

When 24.34 g (0.10 mole) of N-(2,2,6,6-tetramethyl-4-piperidyl)-N'-(2-hydroxymethyl)-ethylenediamine are reacted with 20.23 g (0.10 mole) of dimethyl suberate, as described in Example 1, 17.0 g of a yellowish resin is obtained.

EXAMPLE 12

A solution of 24.34 g of N-(2,2,6,6-tetramethyl-4-piperidyl)-N'-(2-hydroxyethyl)-ethylenediamine and 19.42 g (0.16 mole) of dimethyl phthalate in 140 ml of xylene is heated for 2 hours. During this time, 70 ml of xylene is removed by distillation. 0.5 g of titanium (IV) butoxide is added and the temperature raised to 160° C., methanol being distilled off slowly. The mixture is stirred for a further 8 hours at 190° C. until 1.4 ml of methanol has been collected.

The product is then dissolved in 100 ml of tetrahydrofuran and precipitated by addition of hexane. The polyesteramide is isolated as semi-solid material, 11,7 g, with an average molecular weight of about 1,000 (by gel permeation chromatography.

EXAMPLE 13

When 12.20 g (0.05 mole) of N-(2,2,6,6-tetramethyl-4-piperidyl)-N'-(2-hydroxyethyl)-ethylenediamine and 9.70 (0.05 mole) of dimethyl terephthalate are reacted as described in Example 1, a solid is obtained. This product is dissolved in 22 ml of ethanol and precipitated by added 30 ml of xylene to give 12.0 g of a light brown solid, mp 190°–210° C., with an average molecular weight of 950 (by gel permeation chromatography).

EXAMPLE 14

Polypropylene (Hercules Profax 6501) containing 0.1% by weight of calcium stearate, but no antioxidant, is blended with the oligomeric light stabilizers. The mixture is pelletized and extruded at 450° F. (232° C.) into tape with a thickness of 5 mil (0.127 mm), using 4 inch (10.16 cm) film die. The tape is cut into ¼ inch (6.4 mm) wide strips which are then stretched by a 6:1 ratio over Godet rolls at a temperature of 225° F. (107° C.) to give a stretched film tape of 2 mil (0.0508 mm) thickness.

The tape is subjected to light exposure in the Carbon Arc Weatherometer (with spray). After exposure, specimen tensile properties are determined. Hours in the Carbon Arc Weatherometer to give 50% retention of tensile strength is considered as a failure time.

The following results are obtained:

| Compound of Example No. | Hours to Failure (50% Retention of Tenacity, Carbon Arc Weatherometer) |
| --- | --- |
| No Light Stabilizer | 385 |
| 1 | 2,850 |
| 2 | 3,250 |
| 9 | 2,575 |
| 10 | 3,080 |
| 11 | 2,530 |
| 13 | 1,070 |

What is claimed is:

1. An oligomeric esteramide having recurring structural units, jointed in essentially a random fashion, of the formula (A)

$$\pm CO-E_1-CO-N-L-O\pm_{\overline{n}}\pm CO-E_2-CO-N-L-O\pm_{\overline{m}} \quad (A)$$
$$\qquad\qquad\qquad | \qquad\qquad\qquad\qquad\qquad | $$
$$\qquad\qquad\qquad G \qquad\qquad\qquad\qquad\qquad G$$

wherein

G is a hindered amine radical of formula I or II $$\underset{(I)}{\begin{array}{c}Z_1\\|\\R^1CH_2\diagup\overset{R^1}{\diagdown}CH_2R^1\\CH_3\diagdown\underset{|}{N}\diagup CH_3\\R^2\end{array}} \quad \text{or} \quad \underset{(II)}{\begin{array}{c}Z_2\\|\\CH_3\diagup\overset{N}{\diagdown}CH_3\\R^1CH_2\diagup\diagdown CH_2R^1\\R^1\end{array}}$$

in which $R^1$ is hydrogen or alkyl having 1 to 4 carbon atoms, $R^2$ is hydrogen, alkyl having 1 to 12 carbon atoms, allyl, benzyl, acetyl, acryloyl or cyano, $Z_1$ is a direct bond, $-NHCH_2CH_2-$, $-NHCH_2CH_2CH_2-$ or $-OCH_2CH_2-$, with the heteroatom attached to the piperidyl ring, $Z_2$ is ethylene or trimethylene, $E_1$ and $E_2$ are the same or different and are alkylene having 2 to 12 carbon atoms, o-phenylene, m-phenylene, p-phenylene, 5-norbornen-2,3-diyl or vinylene, L is ethylene, trimethylene or $-CH_2CHR^3-$ where $R^3$ is alkyl having 1 to 6 carbon atoms, cycloalkyl having 5 or 6 carbon atoms or phenyl, the sum of n plus m is 2 to 50, and when $E_1$ and $E_2$ are different, the ratio of n/m is 49/1 to 1/49.

2. An esteramide according to claim 1 wherein G is a hindered amine radical of formula I.

3. An esteramide according to claim 1 wherein $R^1$ is hydrogen or methyl.

4. An esteramide according to claim 1 wherein $R^2$ is hydrogen, methyl, propyl, allyl, benzyl or acetyl.

5. An esteramide according to claim 1 wherein $Z_1$ is a direct bond, $-NHCH_2CH_2-$ or $-OCH_2CH_2-$.

6. An esteramide according to claim 1 wherein $Z_2$ is ethylene.

7. An esteramide according to claim 1 wherein $E_1$ and $E_2$ are the same.

8. An esteramide according to claim 1 wherein $E_1$ and $E_2$ are alkylene of 2 to 8 carbon atoms, o-phenylene, m-phenylene or p-phenylene.

9. An esteramide according to claim 1 wherein L is ethylene, trimethylene, propylene or styrolene.

10. An esteramide according to claim 1, wherein $E_1$ is ethylene, $E_2$ is tetramethylene, L is ethylene, G is formula I, where $R^1$ is hydrogen, $R^2$ is hydrogen, $Z_1$ is a direct bond and the ratio of n/m is 4/1.

11. An esteramide according to claim 1 wherein $E_1$ and $E_2$ are tetramethylene, L is ethylene, G is formula I where $R^1$ is hydrogen, $R^2$ is hydrogen and $Z_1$ is $-NHCH_2CH_2-$.

12. An esteramide according to claim wherein $E_1$ and $E_2$ are tetramethylene, L is trimethylene, G is formula I where $R^1$ is hydrogen, $R^2$ is hydrogen and $Z_1$ is a direct bond.

13. An esteramide according to claim 1 wherein $E_1$ and $E_2$ are ethylene, L is propylene, G is formula I where $R^1$ is hydrogen, $R^2$ is hydrogen and $Z_1$ is a direct bond.

14. A composition of matter comprising an organic material subject to light-induced deterioration stabilized with from 0.05 to 5% by weight of an esteramide according to claim 1.

15. A composition according to claim 14 in which the organic matter is a polyolefin.

16. A composition according to claim 15 wherein the polyolefin is polyethylene.

17. A composition according to claim 15 wherein the polyolefin is polypropylene.

18. A composition according to claim 14 where in the esteramide of formula (A) $E_1$ is ethylene, $E_2$ is tetramethylene, L is ethylene, G is formula I where $R^1$ is hydrogen, $R^2$ is hydrogen, $Z_1$ is a direct bond and the ratio of n/m is 4.1.

19. A method of stabilizing an organic material subject to light-induced deterioration which comprises incorporating in said material from 0.05 to 5% by weight of said material of an esteramide according to claim 1.

20. A method according to claim 19 in which the organic material is a polyolefin.

21. A method according to claim 20 wherein the polyolefin is polyethylene.

22. A method according to claim 20 wherein the polyolefin is polypropylene.

23. A method according to claim 19 where in the esteramide of formula (A) $E_1$ is ethylene, $E_2$ is tetramethylene, L is ethylene, G is formula I where $R^1$ is hydrogen, $R^2$ is hydrogen, $Z_1$ is a direct bond and the ratio of n/m is 4/1.

* * * * *